United States Patent [19]

Simon et al.

[11] Patent Number: 4,851,344
[45] Date of Patent: Jul. 25, 1989

[54] MICROBIAL REDUCTION OF MONOCARBOXYLIC AND DICARBOXYLIC ACIDS IN THE PRESENCE OF CARBON MONOXIDE AND/OR FORMATES PLUS MEDIATORS

[75] Inventors: Helmut Simon; Herbert Lebertz, both of Freising, Fed. Rep. of Germany

[73] Assignee: BASF Aktiengesellschaft, Ludwigshafen, Fed. Rep. of Germany

[21] Appl. No.: 148,640

[22] Filed: Jan. 26, 1988

[30] Foreign Application Priority Data

Feb. 19, 1987 [DE] Fed. Rep. of Germany ....... 3705272

[51] Int. Cl.$^4$ .................. C12P 7/02; C07C 29/13; C07C 31/02; C12R 1/14
[52] U.S. Cl. .................................... 435/155; 435/146; 435/156; 435/157; 435/158; 435/160; 435/161
[58] Field of Search ............... 435/146, 147, 155, 156, 435/157, 158, 160, 161

[56] References Cited

U.S. PATENT DOCUMENTS 4,749,670 6/1988 Simon et al. ...................... 435/158

FOREIGN PATENT DOCUMENTS 1289891 12/1986 Japan .................................. 435/157

OTHER PUBLICATIONS

J. Biol. Chem. 259, (1984), 7109.
Meth. Enzymol. 71, (1981), 263.
J. Biol. Chem. 256, (1981), 9542.
Biochem. Biophys. Acta 665, (1981), 34.
Biotech. 87-02278, Simon et al., NATO AS SerC(1986), 178 Enzymes Catal. Org. Synth. 35–44.
Biotech. 85-02458, Krab et al., Prog. Ind. Microbiol, (1984), 20, Innovations in Biotech 507–16.
Biotech. 84-01272, Krab et al., Biotech Res. Neth., (1983), 174.
Biotech. 82-02515, Popov et al., PBMIAK, (1982), 18 499–507.
Biotech. 88-03056, Rad et al., ACSRAL (Abs. Pap. Amer. Chem. Soc.), (1987), 194 Meeting.

Primary Examiner—Herbert J. Lilling
Attorney, Agent, or Firm—Keil & Weinkauf

[57] ABSTRACT

Monocarboxylic and dicarboxylic acids of up to 10 carbon atoms, which may also contain double bonds and be substituted by halogen, phenyl or hydroxyl, are microbially reduced to the corresponding alcohols by performing the reduction with carbon monoxide and/or a formate in the presence of a mediator.

1 Claim, No Drawings

MICROBIAL REDUCTION OF MONOCARBOXYLIC AND DICARBOXYLIC ACIDS IN THE PRESENCE OF CARBON MONOXIDE AND/OR FORMATES PLUS MEDIATORS

It is known that biological cells reduce unbranched carboxylic acids of a wide range of chain lengths to alcohols. Reactions of this type have been been carried out with bacterial systems (J. Biol. Chem. 259 (1984), 7109 and earlier literature cited therein), vegetable systems (Meth. Enzymol. 71 (1981), 263) and animal systems (J. Biol. Chem. 256 (1981), 9542, and Biochem. Biophys. Acta 665 (1981), 34). In all previously disclosed cases of this reaction, the carboxylate is not reduced as such but as an activated acyl compound with NADH or NADPH. Only by coupling with a high-energy compound is it possible to accomplish the reaction $$RCOO^- + 2NAD(P)H + 3H^+ \rightarrow RCH_2OH + 2NAD(P)^+ + H_2O$$

which is endogonic at 6.8 kcal/mol.

We have found that carboxylic acids can be reduced to the corresponding alcohols in a simple manner.

The present invention accordingly provides a process for the microbial reduction of a monocarboxylic or dicarboxylic acid of up to 10 carbon atoms, which may also contain double bonds and be substituted by halogen, phenyl or hydroxyl, to the corresponding alcohol by performing the reduction with carbon monoxide and/or a formate in the presence of a mediator.

Monocarboxylic and dicarboxylic acids which are particularly suitable for the reaction are saturated monobasic carboxylic acids, eg. acetic acid, propionic acid, butyric acid, 2-methylbutyric acid, n-pentanoic acid and n-hexanoic acid, saturated dicarboxylic acids, eg. succinic acid, glutaric acid, adipic acid and suberic acid, unsubstituted or alkyl-substituted benzoic acid, phthalic acids, terephthalic acid, aliphatic/aromatic carboxylic acids, eg. 2- and 3-phenylbutyric acid, cinnamic acid and cyclohexanecarboxylic acid. Suitable substituted carboxylic acids are in particular hydroxylated and chlorinated carboxylic acids, eg. lactic acid and 3-chloropropionic acid.

Suitable microorganisms for the reduction are for example Clostridium thermoaceticum (DSM 521), Clostridium aceticum (DSM 1496), Chlostridium formicoaceticum (DSM 92) and Butyribacterium methylotrophicum (DSM 3468). These microorganisms are particularly highly suitable for the reduction. The reduction is also possible with Acetobacterium woodii (DMS 1030), Desulfobacterium autotrophicum (DSM 3382) and Eubacterium limosum (DSM 20402). Further suitable microorganisms can be determined by simple testing.

The microorganisms can be used for the reduction directly, as crude extracts or in immobilized form.

Suitable mediators are the following substances:
1. vilogen dyes, eg. methylviologen, benzylviologen, diquat,
2. anthraquinone and other quinone dyes, eg. phenosafranine, anthraquinonesulfonic acids,
3. triphenylmethane dyes, eg. methyl violet, crystal violet,
4. phthalocyanines, eg. Fe phthalocyanine, Cu phthalocyanine or Co phthalocyanine,
5. methine dyes, for example astraphloxine,
6. pyrrole dyes or porphyrin dyes, eg. metal chelate complexes thereof,
7. pteridines and pteridones,
8. flavines, eg. acriflavine, lumiflavine,
9. metal complexes of the metals of secondary groups VI, VII and VIII, eg. Ru(L$_2$L'$_2$)$^{++}$[L=1,10-phenanthroline, 2,2-bipyridyl or 5-nitro-1,10-phenanthroline; L'=pyridine or 4-methylpyridine], 1,1'-bis(hydroxymethyl)ferrocenes and ferrocenemonocarboxylic acids.

Of these, preference is given to the 1st group, in particular methylviologen and benzylviologen.

Suitable mediators also include certain metal complexes such as cobalt sepulchrate.

The novel process is preferably carried out in a buffer at from 30° to 60° C. Advantageously, a pH from about 5 to 6 is employed. The carbon monoxide can be introduced into the reaction vessel, or the reaction batch is subjected to shaking in a carbon monoxide atmosphere.

If the novel process is employed for reducing racemic acids, in general one antipode of the racemate is more rapidly converted into the alcohol than the other. It is therefore possible to obtain a substantial excess of one antipode in the end product by terminating the reaction before it has run its course.

The novel process has the advantage that the carboxylic acid can be reduced under gentle conditions, without activation, in a substantially neutral pH range and at room temperature. The process requires no cofactors which are difficult to regenerate.

EXAMPLE 1

Typical reduction of saturated carboxylic acids with carbon monoxide.

30 mg (dry weight) of Clostridium thermoaceticum (DSM 521), 1 mmol of methylviologen and 70 μmol of carboxylic acid salt were introduced in 1 ml of 0.2M potassium phosphate buffer of pH 5.5. The batch was shaken at 40° C. in a CO atmosphere. The progress of the reaction was monitored by gas chromatography on small aliquot samples. The reaction was discontinued when no carboxylic acid was detectable any longer.

In this way the following substrates produced the following end products in a substantially quantitative yield:

| Substrate | Product |
|---|---|
| acetate | ethanol |
| propionate | 1-propanol |
| n-butyrate | 1-butanol |
| n-pentanate | 1-pentanol |
| n-hexanate | 1-hexanol |
| succinate | 1,4-butanediol |
| glutarate | 1,5-pentanediol |
| adipate | 1,6-hexanediol |
| suberate | 1,8-octanediol |
| benzoic acid | benzyl alcohol |
| (2R,S)-phenylbutyrate | 2-phenylbutanol |
| (R)-lactate | 1,2-propanediol |
| (S)-lactate | 1,2-propanediol |
| (E)-2-methyl-2-butenoate | 2-methyl-2-butenol |
| (E)-2-methylcinnamate | (2R)-2-methyl-3-phenyl-propionate |
| vinyl acetate | 3-buten-1-ol |
| sorbate | sorbinol and E-4-hexen-1-ol |

EXAMPLE 2

Example 1 was repeated to reduce (R,S)-2-phenylbutyrate to 2-phenylbutanol. The reaction was discontinued when 40% of the starting material had been converted. The 2-phenylbutanol thus obtained had an angle of rotation of $[\alpha]^D$ of $+10.2°$ in pentane (an angle of rotation of $+16.5°$ has been reported for the pure S form; cf. Soc. Chim. France 634 (1967), 613).

Example 3

To immobilize Clostridium thermoaceticum, 1.0 g of wet-pack cells, suspended in 1.5 ml of 0.1M potassium phosphate buffer of pH 7.0, was introduced in 5 ml of a 3% strength solution of K-carrageenan in 0.9% of sodium chloride at 55° C. in the air. After brief stirring the mixture was introduced into a Petri dish 9 cm in diameter and allowed to solidify at room temperature. To immobilize the gel further, it was coated for 30 min with a 2% potassium chloride solution. A portion of the gel containing about 0.4 g of cells converts 84 μmol of propionate to propanol under the conditions specified in Example 1 within 23 h.

We claim:

1. A process for the microbial reduction of a monocarboxylic or dicarboxylic acid of up to 10 carbon atoms, which may also contain double bonds and be substituted by halogen, phenyl or hydroxyl, to the corresponding alcohol by performing the reduction with carbon monoxide and/or a formate in the presence of a mediator.

* * * * *